(12) United States Patent
Hayes

(10) Patent No.: US 10,500,401 B2
(45) Date of Patent: Dec. 10, 2019

(54) NETWORK COMMUNICATION FOR PATIENT SUPPORT APPARATUSES

(71) Applicant: Stryker Corporation, Kalamazoo, MI (US)

(72) Inventor: Michael Joseph Hayes, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 0 days.

(21) Appl. No.: 15/831,466

(22) Filed: Dec. 5, 2017

(65) Prior Publication Data

US 2018/0154162 A1 Jun. 7, 2018

Related U.S. Application Data

(60) Provisional application No. 62/430,500, filed on Dec. 6, 2016.

(51) Int. Cl.
*A61N 1/372* (2006.01)
*G01S 5/02* (2010.01)
(Continued)

(52) U.S. Cl.
CPC ........ *A61N 1/37282* (2013.01); *G01S 5/0221* (2013.01); *G06F 1/163* (2013.01);
(Continued)

(58) Field of Classification Search
None
See application file for complete search history.

(56) References Cited

U.S. PATENT DOCUMENTS

| 6,078,261 A | * | 6/2000 | Davsko | ................. A61B 5/1115 200/85 R |
| 6,344,794 B1 | * | 2/2002 | Ulrich | ................ G06K 17/0022 340/539.13 |

(Continued)

FOREIGN PATENT DOCUMENTS

| WO | 2007018566 A2 | 2/2007 |
| WO | 2015170253 A1 | 11/2015 |
| WO | 2017124056 A1 | 7/2017 |

OTHER PUBLICATIONS

"5G" published by Wikipedia at https://en.wikipedia.org/wiki/5G and last modified on Nov. 2, 2016.

(Continued)

*Primary Examiner* — Curtis J King
(74) *Attorney, Agent, or Firm* — Warner Norcross + Judd LLP

(57) ABSTRACT

Patient support apparatuses, such as beds, cots, stretchers, chairs, or the like, include wireless communication systems that are adapted to communicate with a non-local wireless receiver positioned outside of the healthcare facility and not associated with the healthcare facility. A computer positioned within the healthcare facility and coupled a local area network of the healthcare facility receives messages from the patient support apparatuses that have been forwarded by the non-local wireless receiver to the local area network. In some embodiments, the wireless receiver is local and positioned within the healthcare facility. In such instances, a second computer, such as a server, forwards a first subset of the patient support apparatus messages to a first computer via the local area network and a second subset of the patient support apparatus messages to a device remote from the healthcare facility. Patient support apparatuses that communicate using visible light are also disclosed.

13 Claims, 7 Drawing Sheets

(51) Int. Cl.
*H04M 1/725* (2006.01)
*G06F 1/16* (2006.01)
*G08B 21/04* (2006.01)
*G08B 25/08* (2006.01)
*H04W 84/18* (2009.01)
*G08B 25/01* (2006.01)
*H04W 84/10* (2009.01)

(52) U.S. Cl.
CPC ..... *G08B 21/0453* (2013.01); *G08B 21/0461* (2013.01); *G08B 25/08* (2013.01); *H04M 1/72536* (2013.01); *G08B 25/016* (2013.01); *H04W 84/10* (2013.01); *H04W 84/18* (2013.01)

(56) References Cited

U.S. PATENT DOCUMENTS

| | | | |
|---|---|---|---|
| 7,242,308 B2 | 7/2007 | Ulrich et al. | |
| 8,082,160 B2 | 12/2011 | Collins, Jr. et al. | |
| 8,319,633 B2 | 11/2012 | Becker et al. | |
| 8,334,777 B2* | 12/2012 | Wilson | G05B 19/042 340/286.07 |
| 8,733,641 B1 | 5/2014 | Drew et al. | |
| 9,320,662 B2* | 4/2016 | Hayes | A61G 7/002 |
| 9,966,997 B2* | 5/2018 | Hayes | H04B 5/0037 |
| 2006/0279427 A1* | 12/2006 | Becker | A61B 5/0002 340/573.4 |
| 2007/0010719 A1* | 1/2007 | Huster | G06F 19/3418 600/300 |
| 2007/0163045 A1* | 7/2007 | Becker | A61B 5/1115 5/616 |
| 2007/0164871 A1* | 7/2007 | Dionne | A61G 7/015 340/573.1 |
| 2007/0210917 A1* | 9/2007 | Collins, Jr. | A61B 5/1117 340/539.1 |
| 2008/0120784 A1* | 5/2008 | Warner | A61B 5/0002 5/658 |
| 2011/0074571 A1 | 3/2011 | Collins, Jr. et al. | |
| 2011/0247139 A1* | 10/2011 | Tallent | A61G 7/018 5/613 |
| 2012/0137436 A1* | 6/2012 | Andrienko | A61G 7/018 5/600 |
| 2014/0080413 A1* | 3/2014 | Hayes | H04B 5/0037 455/41.1 |
| 2014/0115784 A1* | 5/2014 | Johannigman | A61G 7/018 5/600 |
| 2014/0184409 A1* | 7/2014 | Vanderpohl, III | A61G 7/05 340/539.22 |
| 2014/0236629 A1* | 8/2014 | Kim | G06Q 50/24 705/3 |
| 2014/0259414 A1* | 9/2014 | Hayes | A61B 5/6892 5/611 |
| 2014/0297327 A1* | 10/2014 | Heil | G06Q 50/22 705/3 |
| 2015/0033295 A1* | 1/2015 | Huster | G06F 21/44 726/4 |
| 2015/0081335 A1* | 3/2015 | Dixon | G06Q 50/22 705/3 |
| 2015/0109442 A1* | 4/2015 | Derenne | G16H 80/00 348/143 |
| 2016/0140307 A1* | 5/2016 | Brosnan | G06F 19/3406 600/324 |
| 2016/0213537 A1* | 7/2016 | Hayes | G06Q 50/22 |
| 2017/0027787 A1* | 2/2017 | Huster | A61B 5/1115 |
| 2017/0099198 A1 | 4/2017 | Bhimavarapu et al. | |
| 2017/0124844 A1* | 5/2017 | Huster | A61G 7/0524 |
| 2017/0270261 A1* | 9/2017 | Contolini | G06F 19/00 |
| 2018/0039743 A1* | 2/2018 | Dixon | G06Q 50/22 |

OTHER PUBLICATIONS

"Li-Fi" published by Wikipedia at https://en.wikipedia.org/wiki/Li-Fi and last modified on Nov. 20, 2016.

* cited by examiner

NETWORK COMMUNICATION FOR PATIENT SUPPORT APPARATUSES

CROSS-REFERENCE TO RELATED APPLICATIONS

This application claims priority to U.S. provisional patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference.

BACKGROUND

The present disclosure relates to patient support apparatuses, such as beds, cots, stretchers, chairs, and the like, that are used in residential and/or medical facilities, such as hospitals and the like.

Medical facilities often use a plurality of devices that communicate wirelessly with one or more local area networks of the medical facilities. Such communication often includes WiFi communication, Bluetooth communication, and/or other wireless protocols. In order to implement such communication with the local area network, the facility's technicians who oversee the administration of the local area network have to configure, set up, and oversee the medical devices' usage of the local area network. In some situations, bandwidth limitations and/or interference issues may impede or prevent successful wireless access to the local area network.

SUMMARY

According to one or more aspects of the present disclosure, improved communication systems are provided that relieve the burden of connecting to, utilizing, and/or managing communications between one or more medical devices and the healthcare facility's local area network. In some embodiments, one or more patient support apparatuses are provided that communicate with one or more devices that are independent of the healthcare facility's local area network. The devices forward all or a subset of the data they receive to the local area network and/or to a network remote from the healthcare facility. In some embodiments, the devices include a patient support apparatus server that receives data from the patient support apparatuses without the data passing through the local area network. After receipt of the data by the patient support apparatus server, such data may be forwarded over the local area network by the patient support apparatus server to any software applications and/or servers that are coupled to the local area network and that request the data. In some embodiments, one or more segments of the communications between the medical devices and the local area network utilize visible light communications whereby messages are transmitted using visible light waves as carriers of such messages. The various communication systems provide different manners for transmitting at least some messages that bypass all or a portion a healthcare facility's local area network, thereby relieving administrative and/or communication burdens associated with using the local area network.

According to a first embodiment, a system is provided that includes a patient support apparatus and a computer, both of which are positioned within a healthcare facility. The patient support apparatus includes a wireless transmitter adapted to communicate with a wireless receiver positioned outside of the healthcare facility and not associated with the healthcare facility. The computer is coupled to a local area network of the healthcare facility and is adapted to receive information from the patient support apparatus that has been transmitted to the wireless receiver and forwarded by the wireless receiver to the local area network.

According to other aspects, the wireless receiver is coupled to a cell phone tower and is in communication with the Internet.

In at least one embodiment, the information transmitted from the wireless receiver to the computer is transmitted without passing through the local area network.

In some embodiments, the computer transmits at least a portion of the information over the local area network to a second computer.

The patient support apparatus is configured in some embodiments to send data to the wireless receiver via the wireless transmitter that is not forwarded to the computer, but instead is forwarded to another computer positioned outside of the healthcare facility. The another computer may be an Internet-accessible server. Further, the data may include diagnostic information relating to a motor on the patient support apparatus.

The transmitted information includes at least one of the following: a status of a brake of the patient support apparatus, a status of a siderail of the patient support apparatus, a weight of an occupant of the patient support apparatus, a height of a support surface of the patient support apparatus, a state of an exit detection system of the patient support apparatus, or other information about the patient support apparatus.

According to another embodiment of the disclosure, a communication system is provided for use in a healthcare facility having a local area network, a first computer coupled to the local area network, and at least one patient support apparatus that has a wireless transmitter. The communication system includes a wireless receiver and a second computer. The wireless receiver is located within the healthcare facility and adapted to receive a set of patient support apparatus data directly from the wireless transmitter of the patient support apparatus without the set of patient support apparatus data traveling through the local area network. The second computer communicates with the local area network, the wireless receiver, and a device remote from the healthcare facility. The second computer also forwards a first subset of the set of patient support apparatus data to the first computer via the local area network and forwards a second subset of the set of patient support apparatus data to the device remote from the healthcare facility.

In other aspects, the computer is adapted to forward the second subset of patient support apparatus data to the device remote from the healthcare facility without forwarding the second subset of patient support apparatus data through the local area network.

The first subset of the patient support apparatus data may include at least one of the following: (a) a status of a brake of the patient support apparatus; (b) a status of a siderail of the patient support apparatus; (c) a weight of an occupant of the patient support apparatus; (d) a height of a support surface of the patient support apparatus; and (e) a state of an exit detection system of the patient support apparatus.

The second subset of the patient support apparatus data may include at least one of the following: (a) a number of times a motor on the patient support apparatus has been operated; (b) a current draw of a motor on the patient support apparatus; (c) a temperature of a component on the patient support apparatus; (d) an error signal from a component of the patient support apparatus; (e) a position of an actuator of the patient support apparatus, and (f) a software and/or hardware version of a component of the patient support apparatus. In other embodiments, the second subset includes one or more items of data relating to the status of one or more pieces of hardware on the patient support apparatus.

The device remote from the healthcare facility is a receiver coupled to a cell phone tower or an Internet-accessible server, in some embodiments. In some of these embodiments, the second computer is adapted to send the second subset of the patient support apparatus data to a receiver of a cell phone tower that forwards the second subset of patient support apparatus data to the Internet-accessible server.

The first subset and the second subset of the patient support apparatus data may include some data common to both subsets, or the two subsets may have mutually exclusive data.

According to still another embodiment of the disclosure, a patient support apparatus is provided. The patient support apparatus is used in a healthcare facility having a local area network with a wireless access point, a computer coupled to the local area network, and at least one network appliance adapted to communicate with both the local area network and a device remote from the healthcare facility. The patient support apparatus comprises a support surface adapted to support a patient thereon, a wireless transmitter, and a controller. The wireless transmitter transmits data to the device remote from the healthcare facility or to the wireless access point. The transmitted data is thereafter forwarded to the computer. The controller controls when the wireless transmitter transmits data to the device remote from the healthcare facility and when the wireless transmitter transmits data to the wireless access point.

According to other aspects, the receiver communicates with the controller and the controller is adapted to transmit data to the wireless access point when the receiver detects a wireless signal from the wireless access point.

In some embodiments, the patient support apparatus includes a visible light emitter and the controller is further adapted to send the data to the remote device using visible light.

According to still another embodiment, a patient support apparatus is provided that includes a frame, a support surface, a visible light emitter, and a controller. The support surface is supported by the frame and adapted to support a patient thereon. The controller is adapted to send a message to a device positioned off-board the patient support apparatus using the visible light emitter.

According to other aspects, the patient support apparatus further comprises a visible light detector adapted to receive a message from the device position off-board the patient support apparatus using.

In some embodiments, the visible light emitter includes at least one Light Emitting Diode (LED). When at least one LED is included, the visible light emitter may include a combination of at least one red LED, one green LED, and one blue LED. When such LEDs are included, the controller may be adapted to send the message to the device positioned off-board the patient support apparatus by varying an intensity level of each of the red LED, green LED, and a blue LED such that a collective color emitted by the visible light emitter varies in a particular manner that is based on a content of the message.

In other embodiments, the controller sends the message to the device positioned off-board the patient support apparatus by turning on and off the LED in a particular sequence that is based on a content of the message.

In any of the embodiments disclosed herein, the wireless transmitter may include an RF transmitter adapted to transmit in at least one of the following frequency bands: 28 Gigahertz, 37 Gigahertz, and 39 Gigahertz.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
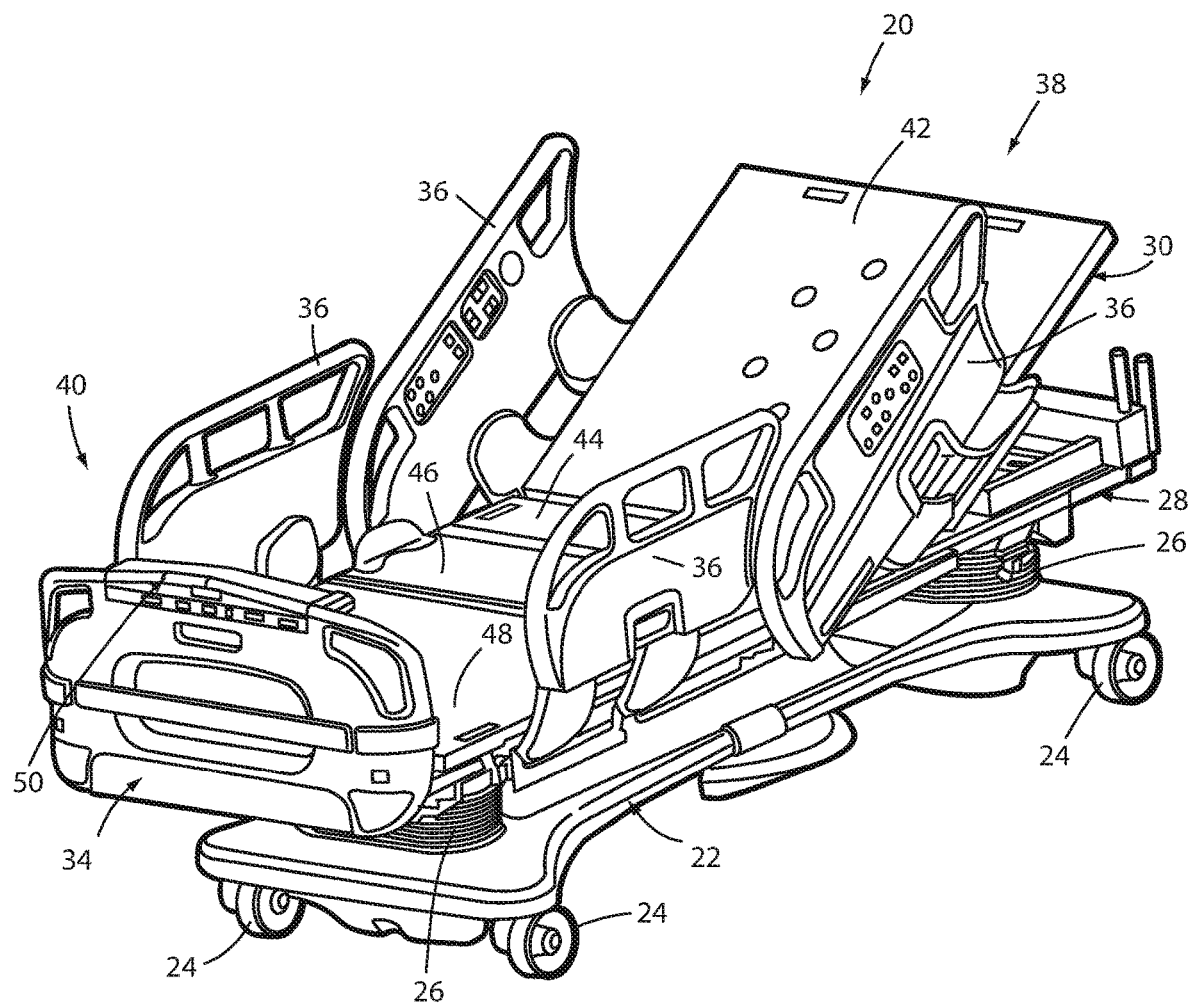
FIG. 1 is a perspective view of a patient support apparatus according to one embodiment of the disclosure.

An illustrative patient support apparatus 20 that incorporates various aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, an operating table, a residential bed, or any other structure capable of supporting a person, whether stationary or mobile and/or whether medical or residential.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard (not shown), a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, pneumatic actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Litter frame 28 is supported by two lift header assemblies (not shown) positioned on top of lifts 26. Each lift header assembly includes a pair of force sensors, which may be load cells, or other types of force sensors, such as, but not limited to, linear variable displacement transducers and/or any one or more capacitive, inductive, and/or resistive transducers that are configured to produce a changing output in response to changes in the force exerted against them. The force sensors are adapted to detect the weight of not only those components of patient support apparatus 20 that are supported by litter frame 28 (including litter frame 28 itself), but also any objects or persons who are wholly or partially being supported by support deck 30. As will be discussed in greater detail below, these force sensors may be part of an exit detection system and/or a scale system of patient support apparatus 20.

The mechanical construction of patient support apparatus 20 may be the same as or similar to the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Patient support apparatuses 20 may also or alternatively be implemented as stretchers, cots, recliners, non-reclining chairs, operating tables, or in other manners. When implemented as a stretcher or cot, patient support apparatuses 20 may be constructed in any of the manners disclosed in commonly assigned U.S. Pat. No. 8,051,511 issued to Nahavandi et al. on Nov. 8, 2011 and entitled EMERGENCY STRETCHER; or commonly assigned U.S. Pat. No. 5,537,700 issued to Way et al. on Jul. 23, 1996 and entitled EMERGENCY STRETCHER WITH X-FRAME SUPPORT, the complete disclosures of both of which are hereby incorporated by reference herein. When patient support apparatus 20 is implemented as a recliner, it may be constructed in any of the manners disclosed in commonly assigned U.S. patent application Ser. No. 14/212,253 filed Mar. 14, 2014 by inventors Christopher Hough et al. and entitled MEDICAL SUPPORT APPARATUS, the complete disclosure of which is also incorporated herein by reference. Still other constructions of patient support apparatuses 20 may be used when one or more of the patient support apparatuses 20 are implemented as cots, stretchers, and/or recliners.

Patient support apparatus 20 further includes a user interface 50 that enables a user of patient support apparatus 20 to control one or more aspects of patient support apparatus 20. User interface 50 is implemented in the embodiment shown in FIG. 1 as a control panel having a lid (flipped down in FIG. 1) underneath which is positioned a plurality of controls. The controls may be implemented as buttons, dials, switches, or other devices. User interface 50 may also include a display for displaying information regarding patient support apparatus 20. The display is a touchscreen in some embodiments. Although FIG. 1 illustrates user interface 50 mounted to footboard 34, it will be understood that user interface 50 can be positioned elsewhere, and/or that one or more additional user interfaces can be added to patient support apparatus 20 in different locations, such as the siderails 36, for controlling various aspects of patient support apparatus 20.

Figure 2:
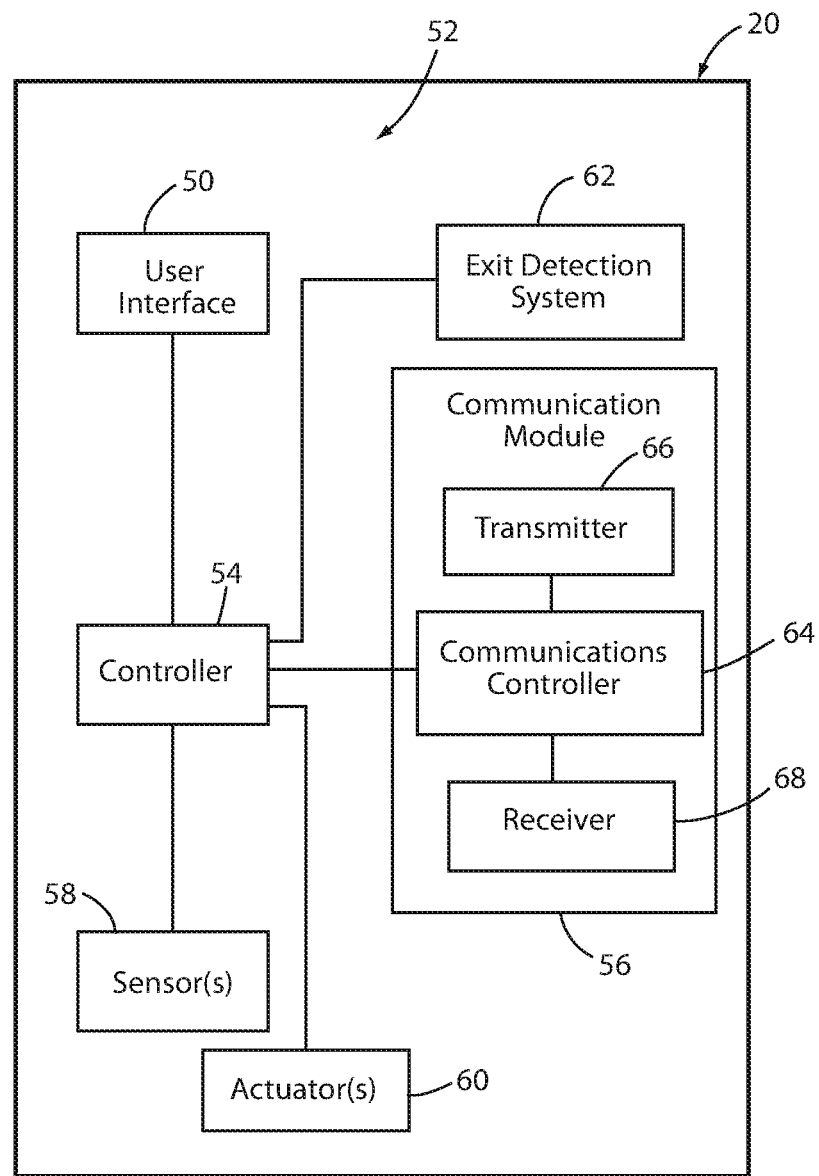
FIG. 2 is a block diagram of the patient support apparatus of FIG. 1.

FIG. 2 illustrates one example of a control system 52 for patient support apparatus 20. Control system 52 includes user interface 50, a main controller 54, a communication module 56, one or more sensors 58, one or more actuators 60, and, in some embodiments, an exit detection system 62. Communication module 56 includes a communications controller 64, a transmitter 66, and a receiver 68. Main controller 54 and communication controller 64 are implemented, in at least one embodiment, as microcontrollers. In one example, main controller 54 and communication controller 64 are each implemented as any one of the i.MX family of system-on-chip (SoC) processors which are marketed by Freescale Semiconductor of Austin, Tex. Other types of commercially available microcontrollers may also be used. Still further, controllers 54 and 64 may take on still other forms, such as any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 54 and 64 in carrying out the functions described herein, as well as the data necessary for carrying out these functions, are stored in one or more accessible memories (not shown).

Controllers 54 and 64 communicate with each other and the other components of control system 52 via one or more conventional protocols, such as, but not limited to, a Controller Area Network (CAN) bus, a Local Interconnect Network (LIN) bus, Firewire, I-squared-C, RS-232, RS-485, a Universal Serial Bus (USB), and/or a Serial Peripheral Interface (SPI) bus. In some embodiments, communication between controllers 54 and 64 and/or between one or more other components of control system 52 takes place via an Ethernet connection. When such an Ethernet connection is used, it may be implemented in any of the manners disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is hereby incorporated herein by reference. Other types of communication protocols may also be used, including wireless communication.

Main controller 54 (FIG. 2) communicates information to user interface 50 that is to be displayed to a user of patient support apparatus 20. Such information includes, in some instances, information detected by one or more of the sensors 58. User interface 50 forwards command signals and/or messages to patient support apparatus controller 54 in response to the commands input via the controls of user interface 50. Patient support apparatus controller 54 responds to such commands by activating one or more actuators 60, or taking other suitable action in response to the commands.

In some embodiments, the actuators 60 controlled by user interface include multiple motors for moving components of patient support apparatus 20, such as actuators for changing a height and/or angle of deck 30, pivoting one or more components of deck 30, activating or deactivating a brake on patient support apparatus 20, and/or other actions.

Sensors 58 include, in at least some embodiments, one or more sensors for detecting the position of the movable components of patient support apparatus 20 (e.g. lifts 26, actuators 60). The outputs from such sensors are used to enable closed-loop control of the movement of these components. Sensors 58 may also include other sensors that detect parameters unrelated to the movement of a component of patient support apparatus 20.

Exit detection system 62 (FIG. 2), if included as part of patient support apparatus 20, may function as either or both a scale system adapted to measure a weight of an occupant of patient support apparatus 20, and/or an exit detection system adapted to detect when a person on support deck 30 exits, or is about to exit, from patient support apparatus 20. In one embodiment, exit detection system 62 determines a center of gravity of the patient and detects movement of the center of gravity outside of one or more defined zones, as disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, exit detection system 62 operates in one or more of the manners described in either of the following commonly assigned patent applications: U.S. patent application Ser. No. 62/065,242 filed Oct. 17, 2014 by inventors Marko Kostic et el. and entitled PATIENT SUPPORT APPARATUSES WITH MOTION MONITORING; and PCT patent application serial number PCT/US2014/02630 filed Mar. 13, 2014, by applicant Stryker Corporation and entitled PATIENT SUPPORT APPARATUS WITH PATIENT INFORMATION SENSORS. Still other types of exit detection systems 62 and/or algorithms may be used.

Figure 3:
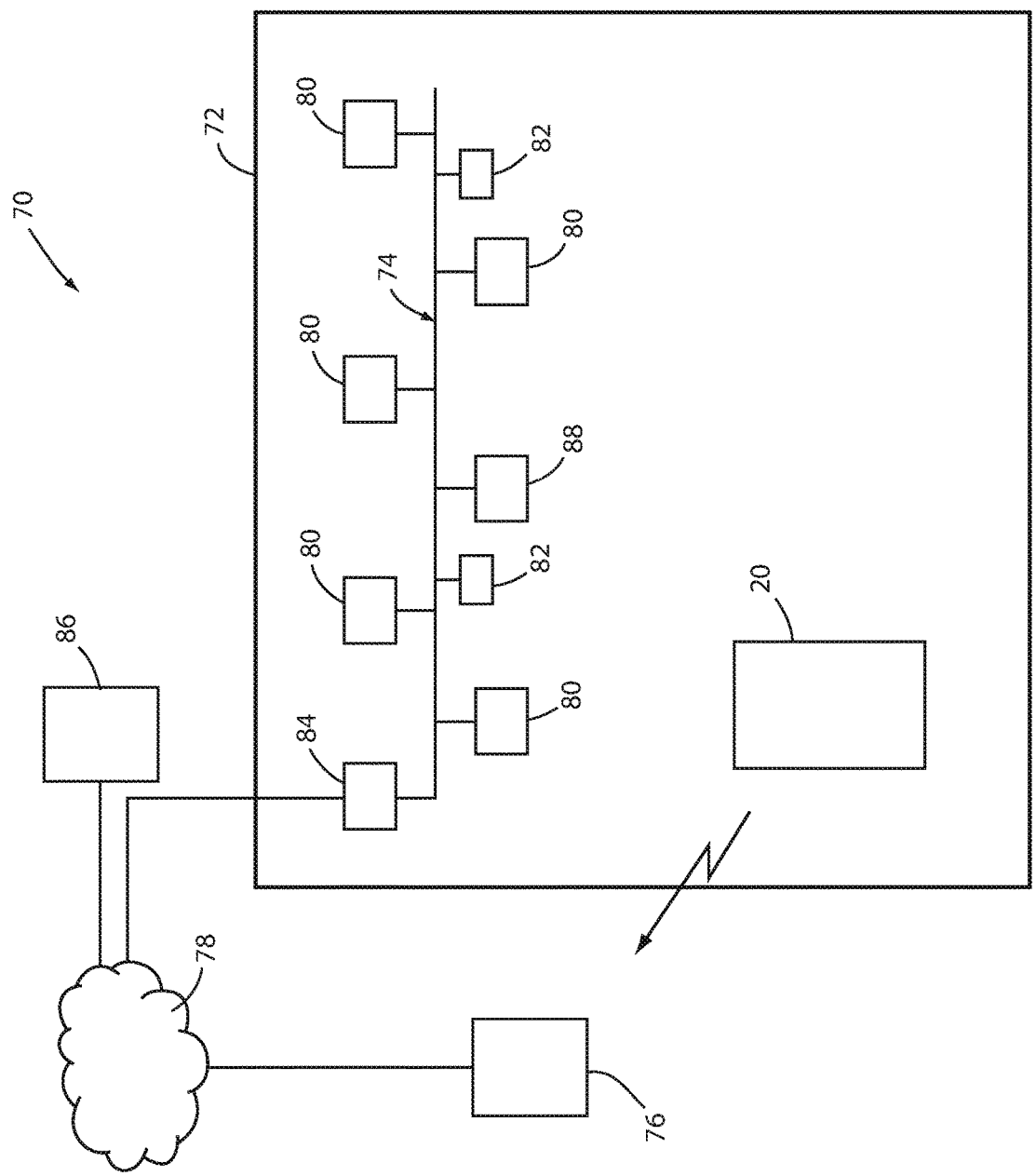
FIG. 3 is a block diagram of a communication system utilizing the patient support apparatus of FIG. 1 according to a first embodiment.

Patient support apparatus 20 may be used with a communications system 70 of the type illustrated in FIG. 3. When used with communications system 70, communication module 56 (FIG. 2) is adapted to wirelessly communicate with one or more remote devices 76 that are positioned outside of a healthcare facility 72 (FIG. 3). Remote devices 76, in at least one embodiment, are cell phone towers that are communicatively coupled to the Internet 78, as will be discussed in more detail below. Healthcare facility 72 may be a hospital, clinic, assisted living home, or other similar type of building. Healthcare facility 72 includes at least one Local Area Network (LAN) 74. LAN 74 is illustrated in FIG. 3 as a single segment, but may include multiple segments or sub-networks, including one or more bridges, switches, routers, or other network appliances that couple the different sections together and forward packets appropriately to their intended destination. Most healthcare facilities 72 include a LAN 74 that is an Ethernet, but it will be understood that communication system 70 is not limited to being implemented with a healthcare facility 72 that includes a LAN 74 implemented as an Ethernet.

As shown in FIG. 3, LAN 74 includes a plurality of computer or servers 80 coupled thereto (the term "computer" is used broadly to encompass both servers and computing devices that are programmed to not act in a server-like manner). LAN 74 may also include one or more wireless access points 82 that are adapted to allow electronic devices positioned within healthcare facility 72 to communicate with LAN 74. In at least one embodiment, wireless access points 82 are adapted to use a WiFi protocol (e.g. IEEE 802.11a, b, g, n, ac, ad, ah, aj, ax, and/or ay) to communicate with one or more electronic devices positioned in healthcare facility 72, such as, but not limited to, one or more medical devices. Other types of protocols, however, can be used for communication between such electronic devices and access points 82 of LAN 74. Indeed, in some embodiments of communication system 70, LAN 74 does not have any wireless access points 82, but instead is only accessible via wired connections.

LAN 74 also includes at least one network appliance 84 that is adapted to communicate with the Internet 78. Network appliance 84 is a conventional router and/or gateway in at least one embodiment. Other types of network appliances 84, however, can be used. Network appliance 84 allows the servers 80 of LAN 74 to communicate with any computers that are Internet-accessible and vice versa.

In the embodiment shown in FIG. 3, communication system 70 also includes an enterprise server 86 that is associated with the manufacturer, seller, and/or distributor of patient support apparatuses 20. Enterprise server 86 is coupled to the Internet 78 and therefore accessible to remote device 76, which is likewise coupled to the Internet 78. Enterprise server 86, in some embodiments, gathers information regarding the use of one or more patient support apparatuses that are present in healthcare facility 72 (and/or other healthcare facilities 72). Such information may include diagnostic information, usage information, and/or servicing information (including requests for servicing), as well as other information regarding patient support apparatuses 20 that is useful to the enterprise associated with patient support apparatuses 20.

Patient support apparatuses 20 communicate with enterprise server 86 via communication module 56. Communication module 56 includes, in some embodiments, a transmitter 66 and a receiver 68 that are both adapted for conventional cellular communication. In some of these embodiments, transmitter 66 and receiver 68 are configured in accordance with the Global System for Mobile Communications (GSM) standard, and communications controller 64 includes a conventional Subscriber Identity Module (SIM) card. In other embodiments, transmitter 66 and receiver 68 are configured in accordance with the Code Division Multiple Access 2000 (CDMA2000) standard. In other embodiments, communications module 56 and transmitter 66 are configured to communicate in accordance with the Universal Mobile Telecommunications System (UTSM) 3G standard and/or the Long Term Evolution (LTE) standard developed by the $3^{rd}$ Generation Partnership Project. In still other embodiments, communications module 56 is configured to communicate in accordance with the LTE Advanced standard, any one or more of the Worldwide Interoperability for Microwave Access (WiMAX) standards, the Evolved High Speed Packet Access (HSPA+) standard, the Fast Low-Latency Access with Seamless Handoff Orthogonal Frequency Division Multiplexing (Flash-OFDM) standard, and/or the IEEE 801.16 standards.

In still other embodiments, communication module 56 is configured to utilize any of the communication techniques currently under consideration for use in 5G communications, such as, but not limited to, the use of Multiple-Input and Multiple-Output (MIMO) methods for multiplying the capacity of radio links. Communication module 56 is configured to operate in any one or more of the following frequency ranges, in at least one embodiment: 28 Gigahertz, 37 Gigahertz, and 39 Gigahertz.

In any of the foregoing embodiments, communication module 56 is configured to have a communication range greater than that of WiFi, thereby enabling communication module 56 to communicate with remote devices 76 that are positioned outside of healthcare facility 72. In some embodiments, communication module 56 uses one or more communication technologies having communication ranges greater than one kilometer. In still other embodiments, communication module 56 is configured to communicate directly with one or more remote devices 76 that are positioned up to several kilometers away from healthcare facility 72, including, but not limited to, distances of greater than ten kilometers.

By allowing patient support apparatus 20 to communicate directly with remote device 76, patient support apparatus 20 is able to communicate with devices outside of healthcare facility 72 without relying upon, connecting to, using, and/or burdening LAN 74. Not only does this reduce the traffic on LAN 74, this also avoids the need for the healthcare facility network administrators to authorize, monitor, and/or maintain communication between patient support apparatuses 20 and LAN 74. Still further, this reduces the total number of devices connected to LAN 74.

Patient support apparatuses 20 are configured in communication system 70 to send data to at least one remote device 76 that is within communication range of patient support apparatus 20. If more than one remote device 76 is within range of a patient support apparatus 20, communication module 56 automatically selects which device 76 to communicate with using the same technology conventional cell phones use to select which cell phone tower to connect to. After establishing a communication connection with remote device 76, controller 54 of patient support apparatus 20 is configured to send one or more pieces of data to remote device 76. Such data includes, in at least one embodiment, data regarding the use and/or status of patient support apparatus 20. For example, in some embodiments, such data includes data regarding the status of any one or more of the following: a height of support deck 30; a position of each siderail 36; a status of a brake for wheels 24 of patient support apparatus 20; a status (armed or disarmed) of exit detection system 62; an angle of support deck 30; whether patient support apparatus 20 is occupied or not; a gross weight, tare weight, and/or patient weight detected by exit detection system 62; and/or any one or more alerts or alarms associated with patient support apparatus 20. Still other types of patient support apparatus date may be transmitted to remote device 76.

The data transmitted to remote device 76 is sent via packets, in at least one embodiment. The layer 3 address of those packets, which are formatted according to the conventional TCP/IP protocols, is not addressed to the remote device 76. Rather, the packets have a layer 2 address that designates the remote device 76. When the remote device 76 receives the packets from a patient support apparatus 20, it strips off the layer 2 address, examines the layer 3 address, and routes the packets in a manner that forwards the packets to the layer 3 address.

In at least one embodiment, the data packets transmitted from patient support apparatus 20 to remote device 76 have an IP address (layer 3) that identifies enterprise server 86. These packets are therefore forwarded by remote device 76 to enterprise server 86. Enterprise server 86 may use these packets for a wide variety of different purpose, including, but not limited to, monitoring the usage of patient support apparatuses 20; scheduling service for patient support apparatuses 20; gathering design, diagnostic, and/or usage data regarding patient support apparatus 20; locating patient support apparatuses 20; retrieving software, firmware, and/or hardware versions currently in use on a patient support apparatus 20; monitoring recalls; and/or for performing other tasks. In some embodiments, patient support apparatuses 20 forward to enterprise server 86 any of the types of information disclosed as being forwarded to the management service disclosed in commonly assigned U.S. patent application Ser. No. 62/361,221 filed Jul. 12, 2016, by inventors David Becker et al. and entitled EQUIPMENT MANAGEMENT SYSTEM, the complete disclosure of which is incorporated herein by reference.

In at least one embodiment, enterprise server 86 is configured to forward a subset of the data received from a patient support apparatus 20 via remote device 76 to the LAN 74 of the corresponding healthcare facility 72. For example, in one embodiment, enterprise server 86 forwards patient support apparatus status data to LAN 74 that may be of interest to healthcare facility personnel, such as, but not limited to, a height of support deck 30, a position of each siderail 36, a status of a brake for wheels 24 of patient support apparatus 20, a status (armed or disarmed) of exit detection system 62, an angle of support deck 30, whether patient support apparatus 20 is occupied or not, a gross weight, tare weight, and/or patient weight detected by exit detection system 62. Enterprise server 86 withholds, in at least one embodiment, forwarding data to LAN 74 that is likely not of interest to healthcare facility personnel. Such information may include diagnostic information, usage information, software, firmware, and/or hardware versions currently in use on a patient support apparatus 20, and/or other information. In some embodiments, enterprise server 86 is configurable by an authorized user to enable the user to custom tailor which data received from the patient support apparatuses 20 via remote device 76 is forwarded to LAN 74 and which data is not forwarded to LAN 74.

Enterprise server 86 forwards data to LAN 74 by sending the data in packets to a patient support apparatus server 88 that is part of LAN 74. Patient support apparatus server 88 is configured to gather data received from the patient support apparatuses 20 located within that particular healthcare facility 72 and share the data with one or more conventional applications executing on any of servers 80 of LAN 74. Depending upon the particular servers installed at a particular healthcare facility 72, patient support apparatus server 88 may therefore communicate with a conventional Admission, Discharge, and Tracking (ADT) server operating on LAN 74 and retrieve information identifying the patient assigned to a particular patient support apparatus 20, and/or forward information regarding the current location of patient support apparatus 20 to the ADT server. Patient support apparatus server 88 may also be in communication with a conventional Electronic Medical Records (EMR) server operating on LAN 74 and both retrieve and write data to the EMR server. As one example, the retrieved data may include data that is displayed by controller 54 on user interface 50 and the written data may include one or more weight readings taken by the scale of exit detection system 62. Other data may also be exchanged with the EMR server. Still further, patient support apparatus server 88 may communicate with one or more conventional work flow servers and/or charting servers that assign, monitor, and/or schedule patient-related tasks to particular caregivers. In some embodiments, patient support apparatus server 88 also communicates with a conventional communication server that forwards communications to particular individuals within healthcare facility 72, such as via one or more portable devices (smart phones, pagers, beepers, laptops, etc.). Patient support apparatus server 88 is configured in some of these embodiments to forward alerts and/or alarms associated with a particular patient support apparatus 20 to the caregiver associated with the patient of that particular patient support apparatus 20.

The forwarding of data from enterprise server 86 to patient support apparatus server 88 is carried out using conventional Internet packet routing. That is, enterprise server 86 sends data in packets that have an IP address corresponding to patient support apparatus server 88. These packets travel through the Internet 78 until they reach network appliance 84 of LAN 74. The network appliance 84 then forwards them to patient support apparatus server 88.

In a modified embodiment of communication system 70, patient support apparatus 20 is modified so that one of controllers 54 and 64 decides what packets are to be sent to enterprise server 86 and to patient support apparatus server 88. In such embodiments, controller 54 or 64 is programmed to analyze the contents of the outgoing data, determine if that data should be sent to enterprise server 86 or patient support apparatus server 88, and address the outgoing data packets according to the selected destination. All of the packets are then initially forwarded to remote device 76 which thereafter routes them in accordance with conventional Internet routing protocols.

In still another modified embodiment of communication system 70, communication module 56 is modified to include WiFi communication abilities, thereby enabling patient support apparatus 20 to directly communicate with one or more of the wireless access points 82 of LAN 74. In some embodiments, an additional communication module is added to patient support apparatus 20 in order to implement this WiFi communication. In other embodiments, the WiFi communication ability is added to communication module 56. Regardless whether communication module 56 or an additional communication module carries out the communication with wireless access points 82, main controller 54 or communication controller 64 is configured to select which communication path to use. That is, controller 54 or 64 analyze the contents of the outgoing data, determine if that data should be sent to enterprise server 86 or patient support apparatus server 88, and adds a layer 2 address to the packets that either identifies remote device 76 or a wireless access point 82. Those packets that are addressed to remote device 76 are intended to be sent to enterprise server 86 and therefore carry a layer 3 address corresponding to server 86. Those packets that are addressed to a wireless access point 82 are intended to be sent to patient support apparatus server 88 and therefore carry a layer 3 address corresponding to server 88. Controller 54 or 64 therefore decides what data to send to which server 86 or 88.

In some embodiments, controller 54 or 64 is programmed to send different data to servers 86 and 88. One such manner of programming controller 54 or 64 involves sending usage and/or diagnostic information to enterprise server 86 and sending status data to patient support apparatus server 88. Other ways of separating the data flows between the servers 86 and 88 may, of course, also or alternatively be implemented. Indeed, in other embodiments, the data sent to each server 86 and 88 is not necessarily mutually exclusive, but includes at least some data that is sent to both server 86 and server 88. Still further, in at least one embodiment, controller 54 or 64 sends the same data to both servers 86 and 88.

In one of the modified embodiments of communication system 70 where patient support apparatus 20 is modified to include WiFi communication abilities, controller 54 or 64 is programmed to take into account network traffic conditions and/or interference possibilities when deciding whether to route data through a wireless access point 82 or a remote device 76. In this embodiment, controller 54 or 64 switches the layer 2 address of at least some traffic destined for patient support apparatus server 88 so as to be routed through remote device 76 if there is excessive traffic through access point 82, potential interference with such traffic, and/or an undesirably weak signal strength. Conversely, if there is excessive traffic, potential interference, weak signal strength, and/or undesirable finance charges (e.g. cellular communications charges) associated with the communication with remote device 76, controller 54 or 64 is programmed to route at least some traffic destined to enterprise server 86 through patient support apparatus server 88. The monitoring of traffic, interference, and/or signal strength may be carried out in accordance with the principles disclosed in commonly assigned U.S. patent application Ser. No. 15/279,918 filed Sep. 29, 2016, by inventors Krishna Bhimavarapu et al. and entitled PERSON SUPPORT APPARATUSES WITH COMMUNICATION CHANNEL MONITORING, the complete disclosure of which is incorporated herein by reference.

Figure 4:
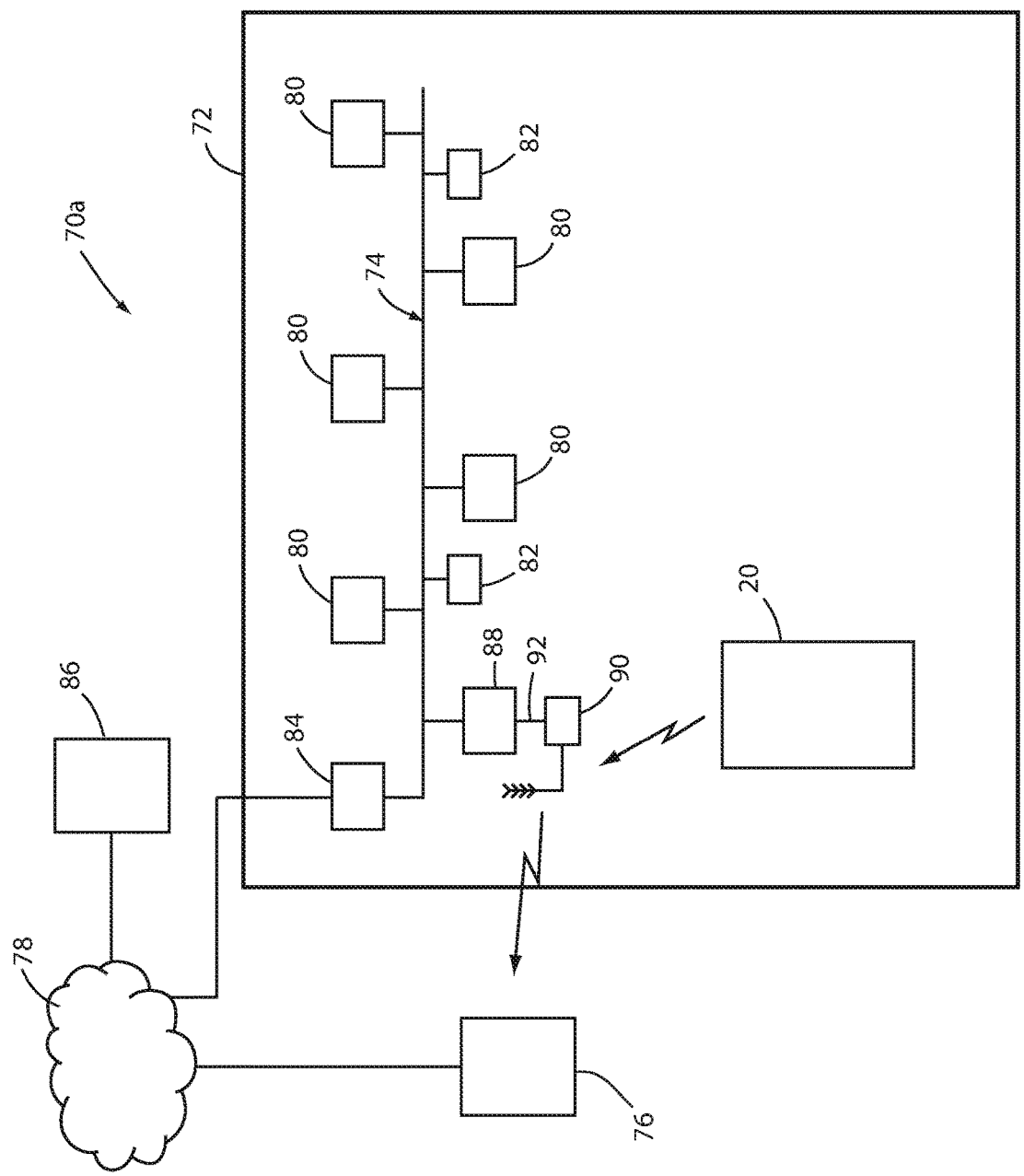
FIG. 4 is a block diagram of an alternative communication system utilizing the patient support apparatus of FIG. 1 according to a second embodiment.

FIG. 4 illustrates an alternative embodiment of a communication system 70a according to the present disclosure. Communication system 70a includes a number of components and/or features that are the same as communication system 70. Those components or features that are common are labeled with the same reference numbers used to describe communication system 70 and, unless otherwise explicitly stated below, operate in the same manner or provide the same function as previously described. Those components or features that are different from communication system 70 are provided with a new reference number and described in more detail below.

Communication system 70a differs from communication system 70 in that the patient support apparatuses 20 within a healthcare facility 72 are able to communicate with patient support apparatus server 88 without utilizing LAN 74 and without routing their data outside of healthcare facility 72. Communication system 70a also differs from communication system 70 in that patient support apparatuses 20 send all of their data destined to either patient support apparatus server 88 or enterprise server 86 to a patient support apparatus server 88, and patient support apparatus server 88 thereafter decides which of the data to send to enterprise server 86 and which of the data to retain and/or make available to the servers 80 on LAN 74. These differences are discussed in greater detail below.

Communication system 70a includes an enterprise receiver 90 communicatively coupled directly to patient support apparatus server 88. Enterprise receiver 90 is an RF receiver that receives RF signals from patient support apparatuses 20 positioned within facility 72. Enterprise receiver 90 is configured to utilize an RF communication protocol that allows for wireless communication over greater distances than WiFi (both 2.4 Gigahertz and 5 Gigahertz), ZigBee, and Bluetooth. In some embodiments, enterprise receiver 90 uses a wireless RF protocol that has a range of at least half a kilometer. Other ranges, however, may be used. In some embodiment, enterprise receiver 90 uses an RF protocol that meets any one or more of the WiMAX standards, the HSPA+ standard, the Flash-OFDM standard, and/or the IEEE 801.16 standard. Still other types of protocols may be used, including, but not limited to, the 5G protocol. The particular protocol that is used by enterprise receiver 90 is also used by the communication modules 56 of patient support apparatuses 20 in system 70a.

Enterprise receiver 90 is configured to allow patient support apparatuses 20 to communicate therewith at substantially any location within healthcare facility 72. This communication ability allows the patient support apparatuses 20 to bypass any existing access points 82 that may be coupled to LAN 74 when communicating with patient support apparatus server 88. As can be seen in FIG. 4, enterprise receiver 90 is coupled to patient support apparatus server 88 via a connection 92. Connection 92 is a wired or wireless connection that is independent of LAN 74. Therefore, when a patient support apparatus transmits a message to enterprise receiver 90, enterprise receiver 90 is able to forward the message to patient support apparatus server 88 without using LAN 74. As a result, patient support apparatuses 20 of FIG. 4 are able to communicate with patient support apparatus server 88 from substantially any location within the healthcare facility without utilizing LAN 74, thereby reducing the load on LAN 74.

Additionally, because communication modules 56 of patient support apparatuses 20 and enterprise receiver 90 use different frequencies for communication than what wireless access points 82 use, potential interference between the communication channels used by access points 82 and the one or more used by enterprise receiver 90 is substantially eliminated. For example, if access points 82 are configured for WiFi access, not only do the patient support apparatuses 20 not count towards the maximum number of clients that a given WiFi access point can communicate with, their wireless communication does not interfere with the WiFi communication.

When enterprise receiver 90 receives a message from a patient support apparatus 20, it delivers the message to patient support apparatus server 88 via connection 92. Patient support apparatus server 88 is configured to determine whether to retain the message, forward the message to enterprise server 86, and/or to forward the message to one or more servers 80 on LAN 74. In some embodiments, patient support apparatus server 88 makes this decision by examining the content of the messages received from the patient support apparatuses 20. For example, patient support apparatus server 88 strips off the header and footers of the packets received from patient support apparatuses 20, regroups the payloads of the packets into complete messages (if the messages span more than one packet), examines the content of the message to determine what type of message it is, looks up stored programming instructions for handling that type of message, and responds according to the stored programming instructions. For some messages, the stored programming instructions instruct server 88 to repacketize the message and send it to remote device 76 for forwarding to enterprise server 86. For other messages, the stored programming instructions instruct server 88 to repacketize the message and send it to a server 80 on LAN 74. For still other messages, the stored programming instructions instruct server 88 to store the contents in a memory of server 88 and make those contents available to a computer (e.g. server 86 and/or a server 80) that subsequently requests them. In some cases, server 88 may take a combination of two or more of these actions in response to certain messages.

In at least one embodiment, patient support apparatus server 88 is configured to sort the set of messages received via enterprise receiver 90 into at least two subsets. The first subset of the messages are forwarded to enterprise server 86 via remote device 76 while the second subset of the messages are forwarded to one or more computers on LAN 74. The first subset of data includes the following: (a) a number of times a motor on the patient support apparatus 20 has been operated; (b) a current draw of a motor on the patient support apparatus 20; (c) a temperature of one or more components of the patient support apparatus 20; (d) an error signal from a component of the patient support apparatus 20; (e) a position of an actuator of the patient support apparatus; (f) a software and/or hardware version of a component of the patient support apparatus; and a location of the patient support apparatus. The second subset of messages includes: (a) a status of a brake of the patient support apparatus; (b) a status of a siderail of the patient support apparatus; (c) a weight of an occupant of the patient support apparatus; (d) a height of a support surface of the patient support apparatus; (e) whether the patient is awake or asleep, (f) whether the patient is one or off of the patient support apparatus; (g) any vital signs of the patient that are detected by the patient support apparatus; (h) a state of an exit detection system of the patient support apparatus; and (i) a location of the patient support apparatus. In some cases, one or more elements of the first or second set are sent to both enterprise server 86 and to one or more computers on LAN 74, such as, but not limited to, location data indicating a location of the patient support apparatus 20. Other manners of sorting the set of messages into two or more subsets may also be implemented. Further, other types of data may be added or substituted into either of these subsets of data.

The communication protocol used between patient support apparatus server 88 and remote device 76 need not be the same protocol used between patient support apparatuses 20 and enterprise receiver 90. However, in some embodiments, enterprise receiver 90 is adapted to use the same protocol for forwarding messages from patient support apparatus server 88 to remote device 76 as was used by patient support apparatuses 20 when sending messages to receiver 90. In still other embodiments, a separate transmitter (not shown) that uses a communication protocol different from that used between patient support apparatuses 20 and patient support apparatus server 88 is coupled to patient support apparatus server 88. This coupling takes place by way of a connection independent of LAN 74. Patient support apparatus server 88 transmits messages that are to be delivered to remote device 76 and enterprise server 86 by sending the messages along that connection to the separate transmitter. As noted, this separate transmitter uses a communication protocol different from what is used for communication between patient support apparatuses 20 and enterprise receiver 90.

Although communication system 70a has been described herein and depicted in FIG. 4 as having a single enterprise receiver 90 positioned with healthcare facility 72, it will be understood that this may be modified in different embodiments. For example, in some embodiments, multiple enterprise receivers 90 are positioned at different locations within healthcare facility 72 and receive wireless messages from the patient support apparatuses 20 positioned within the healthcare facility 72 (or within the vicinity of healthcare facility 72). The precise positions of the enterprise receivers 90 may vary, but are generally chosen so as to ensure that patient support apparatuses 20 are able to communicate with at least one receiver 90 when positioned at any location within the healthcare facility 72. In some instances, the multiple enterprise receivers 90 are positioned close enough to each other in order to communicate with each other wirelessly. In such instances, at least one of the wireless receivers 90 is coupled by a direct connection 92 (wired or wireless) to patient support apparatus server 88. Any of the enterprise receivers 90 that are not directly coupled to patient support apparatus server 88 by connection 92 wirelessly relay the messages they receive from patient support apparatuses 20 to one or more other enterprise receivers 90 until the messages reach an enterprise receiver 90 that has direct connection 92 to patient support apparatus server 88. This relaying of messages takes place without using LAN 74.

In an alternative embodiment, if a patient support apparatus 20 is positioned at a location where is it not able to communicate directly with an enterprise receiver 90, the patient support apparatus 20 is configured to communicate with one or more other patient support apparatuses 20 via one or more mesh networks. This mesh network communication allows an out-of-range patient support apparatus 20 to forward its messages to one or more other patient support apparatuses 20 until the messages reach a patient support apparatus 20 that is positioned within range of enterprise receiver 90. Suitable methods and systems for implementing such mesh network communications in patient support apparatuses are disclosed in commonly assigned U.S. patent application Ser. No. 13/802,855 filed Mar. 14, 2013, by inventors Michael Hayes et al. and entitled PATIENT SUPPORT APPARATUS COMMUNICATION SYSTEMS, the complete disclosure of which is incorporated herein by reference.

Enterprise receiver 90 is programmed in some embodiments of communication system 70a to aggregate multiple messages from patient support apparatuses 20 before sending them to enterprise server 86. This message aggregation is based upon a total number of messages, a total elapsed amount of time since the last aggregated set of messages was previously forwarded to enterprise server 86, a total amount of data in the aggregated messages to enterprise server 86, and/or a combination of these factors. Such message aggregation reduces the frequency at which patient support apparatuses 20 communicate with enterprise server 86. Because remote device 76 is a conventional cellular tower in some embodiments, reducing the number of times that enterprise receiver 90 communicates with the cellular tower can reduce the fees or avoid additional fees associated with the use of the cellular tower (e.g. the cellular fees charged by a telecommunication carried, such as, but not limited to, AT&T, Verizon, Sprint, etc.).

Figure 5:
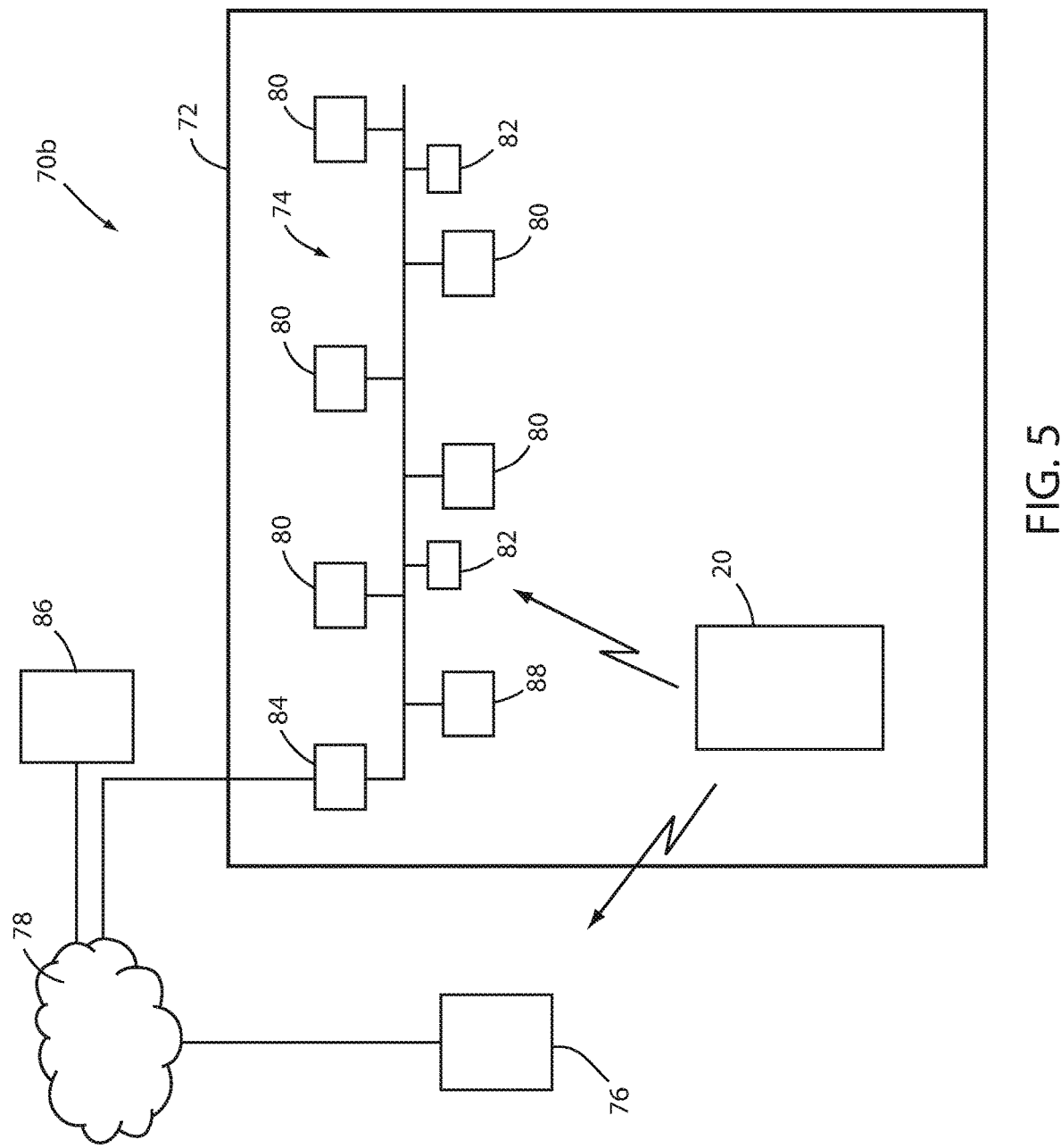
FIG. 5 is a block diagram of another alternative communication system utilizing the patient support apparatus of FIG. 1 according to a third embodiment.

FIG. 5 illustrates an alternative embodiment of a communication system 70b according to the present disclosure. Communication system 70b includes a number of components and/or features that are the same as communication systems 70 and/or 70a. Those components or features that are common are labeled with the same reference numbers used to describe communication systems 70, 70a and unless otherwise explicitly stated below, operate in the same manner or provide the same function as previously described. Those components or features that are different from communication systems 70, 70a are provided with a new reference number and described in more detail below.

Communication system 70b differs from communication system 70a in that the patient support apparatuses 20 within a healthcare facility 72 decide where to send their messages, rather than patient support apparatus server 88. That is, unlike communication system 70a where the patient support apparatuses 20 send all of their messages to an enterprise receiver 90 (or, in the case of a patient support apparatus mesh network, another patient support apparatus 20), the patient support apparatuses 20 of communication system 70b send their messages either to a wireless access point 82 of LAN 74 or to remote device 76. Those messages sent to remote device 76 are forwarded via the Internet 78 to enterprise server 86. The control systems 52 of the patient support apparatuses of communication system 70b are thus programmed with the same message-routing selection instructions as patient support apparatus server 88 of communication system 70a.

In one embodiment, controllers 54 and/or 64 route their outgoing messages as follows. Messages containing any of the following data are sent to remote device 76 for forwarding to enterprise server 86: (a) a number of times a motor on the patient support apparatus 20 has been operated; (b) a current draw of a motor on the patient support apparatus 20; (c) a temperature of one or more components of the patient support apparatus 20; (d) an error signal from a component of the patient support apparatus 20; (e) a position of an actuator of the patient support apparatus 20, and (f) a software and/or hardware version of any one or more components of patient support apparatus 20 that is currently in use. Message containing any of the following data are sent to patient support apparatus server 88 via a wireless access point 82: (a) a status of a brake of the patient support apparatus; (b) a status of a siderail of the patient support apparatus; (c) a weight of an occupant of the patient support apparatus; (d) a height of a support surface of the patient support apparatus; (e) whether the patient is awake or asleep, (f) whether the patient is one or off of the patient support apparatus; (g) any vital signs of the patient that are detected by the patient support apparatus; and (h) a state of an exit detection system of the patient support apparatus. In some instances, patient support apparatuses 20 are programmed to also send some of the aforementioned data to both patient support apparatus server 88 and enterprise server 86.

In at least one embodiment of communication system 70b, patient support apparatuses 20 communicate with wireless access points 82 using WiFi. In other embodiments, patient support apparatuses communicate with LAN 74 via a wired connection, such as, but not limited to, an Ethernet cable. Sill further, in some embodiments, both wireless and wired communication with LAN 74 is carried out by the patient support apparatuses 20.

Communication between patient support apparatuses 20 and remote device 76 in communication system 70b takes place in any of the same manners discussed above with respect to communication system 70. In other words, patient support apparatuses 20 communicate with remote device 76 using any of the same communication protocols and/or standards discussed above that are used between patient support apparatuses 20 and remote device 76 of communication system 70. These include, but are not limited to, the GSM, CDMA2000, UTSM, LTE, LTE Advanced, WiMAX, HSPA+, Flash-OFDM, IEEE 801.16, 2G, 3G, 4G and/or 5G standards.

Although FIG. 5 depicts remote device 76 as being positioned outside of healthcare facility 72, it will be understood that communication system 70b may be modified such that remote device 76 is positioned within healthcare facility. When positioned within healthcare facility 72, remote device 76 acts in a similar fashion to enterprise receiver 90 of system 70a, except that remote device 76 forwards all of its messages via Internet 78 to enterprise receiver 90. Such forwarding takes place by communicating with another remote device 76 positioned outside of healthcare facility 72. The other remote device may be a conventional cellular tower, or other Internet-coupled device. In some instances where a first remote device 76 is positioned within healthcare facility 72, the remote device 76 is programmed to aggregate multiple messages from multiple patient support apparatuses and transmit them as a group to enterprise server 86, thereby reducing how often the cellular tower is accessed, and mitigating fees that may be associated with such communication (e.g. cellular fees charged by a telecommunication carried, such as, but not limited to, AT&T, Verizon, Sprint, etc.).

Figure 6:
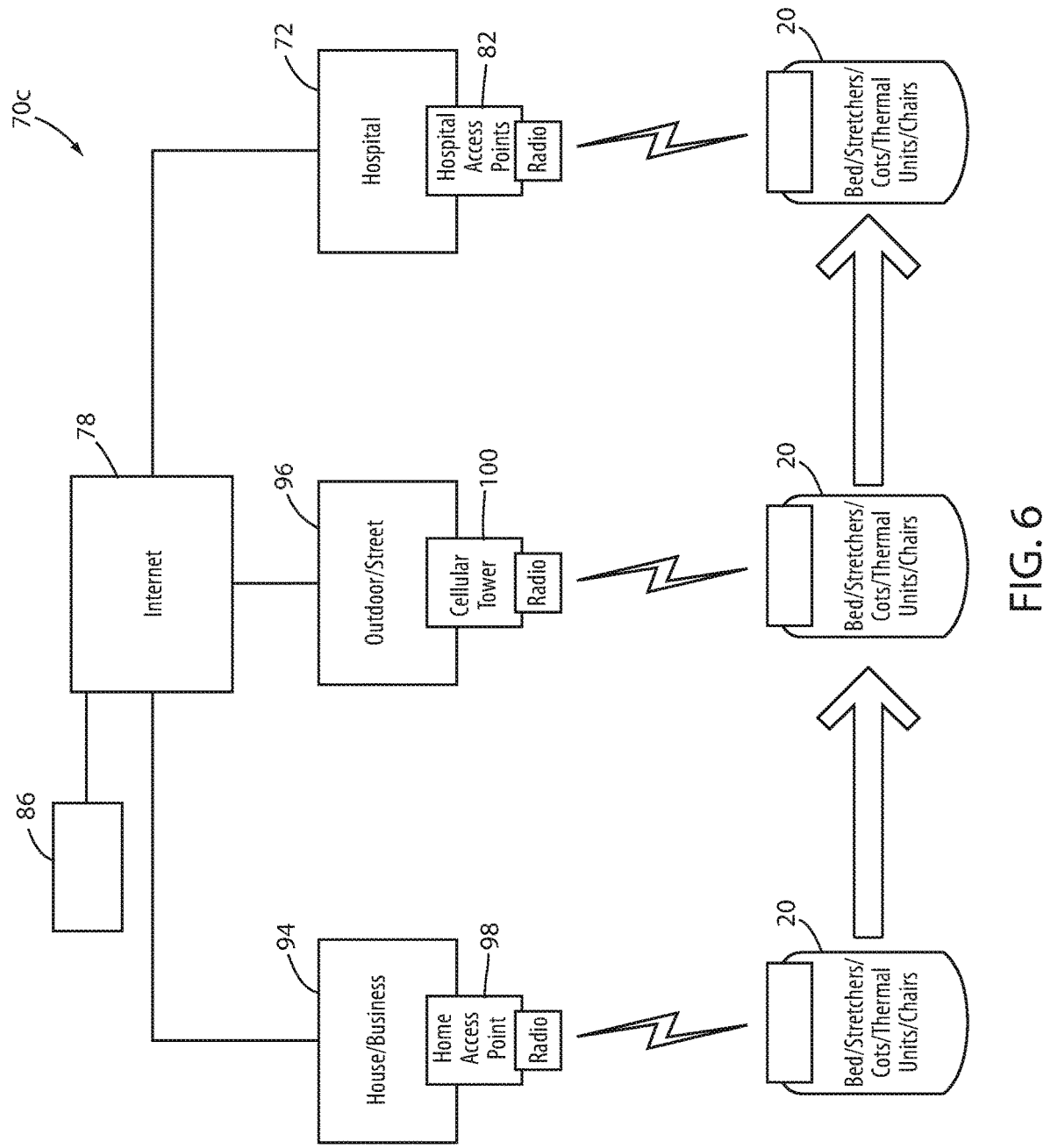
FIG. 6 is a block diagram of yet another alternative communication system utilizing the patient support apparatus of FIG. 1 according to a fourth embodiment.

FIG. 6 illustrates another alternative embodiment of a communication system 70c according to the present disclosure. Communication system 70c includes a number of components and/or features that are the same as communication systems 70, 70a, and/or 70b. Those components or features that are common are labeled with the same reference numbers used to describe communication systems 70, 70a, 70b, and unless otherwise explicitly stated below, operate in the same manner or provide the same function as previously described. Those components or features that are different from communication systems 70, 70a, 70b are provided with a new reference number and described in more detail below.

Communication system 70c includes one or more patient support apparatuses 20 that are adapted to communicate with different entities depending upon their physical location. As shown in FIG. 6, patient support apparatuses 20 may be positioned inside a home or business 94, outdoors 96, or in a healthcare facility 72. When positioned inside a home or business 94, the communication module 56 of the patient support apparatus 20 communicates with a home access point 98. Home access point 98 is any conventional access point that provides Internet access to its connected devices. In some embodiments, home access point 98 is a conventional router coupled to the Internet. Communication between patient support apparatus 20 and home access point 98 may be wireless (e.g. WiFi) and/or it may be wired (e.g. an Ethernet cable).

In some embodiments of communication system 70c, the patient support apparatuses 20 are programmed with an association to a particular healthcare facility 72. In such instances, the patient support apparatuses 20 transmit messages to the patient support apparatus server 88 positioned within the healthcare facility 72 to which the patient support apparatus 20 is associated. This is done by configuring the patient support apparatus 20 with the IP address and/or other identifying information of the patient support apparatus server 88 to which the patient support apparatus 20 is to communicate. Messages destined to server 88 are then sent by patient support apparatus 20 to home access point 98, which forwards them to the Internet 78 and to LAN 74 via the network appliance 84 of LAN 74.

Patient support apparatuses 20 of communication system 70c are also able to communicate with enterprise server 86 when they are positioned inside a home/business 94 (as well as when they are outdoors 96 or within a healthcare facility 72). This is done by configuring the patient support apparatus 20 with the IP address and/or other identifying information of enterprise server 86. Messages destined to server 86 are then sent by patient support apparatus 20 to home access point 98, which forwards them to the Internet 78 and to server 86. As with any of the previously discussed communication systems 70, 70a, and 70b, the communication modules of patient support apparatuses 20 of system 70c are configured to select where to send their messages based upon the content of the messages. Such content-based routing of messages may take place based upon any of the previously defined sets of messages destined for servers 86 and 88.

If patient support apparatus 20 is moved to an outdoor area 96, such as, but not limited to, an ambulance or other patient transport vehicle, patient support apparatus 20 is configured to continue to communicate with both enterprise server 86 and patient support apparatus server 88 via one or more cellular towers 100. Patient support apparatus 20 selects which messages to send to which server 86 and 88 in the same manner as it does when it is positioned within home/business 94.

If patient support apparatus 20 is moved inside of a healthcare facility 72, patient support apparatus 20 is configured to continue to communicate with both enterprise server 86 and patient support apparatus server 88. In the embodiment shown in FIG. 6, patient support apparatus 20 carries out this communication by communicating with one or more access points 82 of the healthcare facility's LAN 74. Messages forwarded to the access points 82 are forwarded to patient support apparatus server 88, which then retains and/or forwards the messages to enterprise server 86 via network appliance 84 and its connection to the Internet 78. It will be understood, however, that communication system 70c can be modified so that the communication between patient support apparatus 20 and patient support apparatus server 88 and/or enterprise server 86 is carried out in one or more of the manners discussed above with respect to communication systems 70, 70a, and 70b.

Patient support apparatuses 20 of communication system 70c automatically determine which entity to communicate with (home access point 98, cellular tower 100, and/or access points 82) based upon their current connectivity status. That is, if patient support apparatus 20 is currently connected to a home or business network via home access point 98, it communicates using access point 98. If it is currently connected to LAN 74 via an access point 82, it communicates using that access point 82. If it is not connected to either of these networks, it communicates via a connection to a cellular tower 100. Communication module 56 automatically switches between these communication methods as the patient support apparatus 20 is moved.

Thus, for example, if patient support apparatus 20 is a cot that is being used to transport a patient from his or her home to healthcare facility 72, the cot initially communicates with home access point 98. As the cot is transported away from home/business 94, the signal strength of the connection between the cot and home access point 98 decreases. This is detected by communication module 56, which switches to communication with cellular tower 100 when the signal strength decreases to below a threshold. As the cot is transported closer and closer to healthcare facility 72, it eventually comes close enough for communication module 56 to detect signals from one or more access points 82. When a signal from at least one access point 82 surpasses a threshold, communication module 56 automatically switches from communicating with cellular tower 100 to communicating with an access point 82. The cot is thereby able to communicate with both servers 86 and 88 at all times throughout the journey from home/business 94 to healthcare facility 72.

The communication between patient support apparatus 20 and patient support apparatus server 88 allows the healthcare facility 72 to receive useful information about the patient prior to the patient arriving at healthcare facility 72. This useful information includes, but is not limited to, one or more of the patient's vital signs, weight, location, medical history, identification, and other information. As discussed, this information is sent to patient support apparatus server 88, which then shares the information with any authorized computing device that is coupled to LAN 74, thereby making the information available to caregivers and other personnel associated with healthcare facility 72.

In some modified embodiments of communication system 70c, the patient support apparatus 20 automatically communicates with cellular tower 100 at locations other than outdoor locations 96. For example, in some embodiments, cellular tower communication happens inside home/business 94 instead of, or in addition to, communication with home access point 98. Further, in some embodiments, cellular tower communication also may happen inside facility 72, instead of or in addition to, communication with access points 82.

Figure 7:
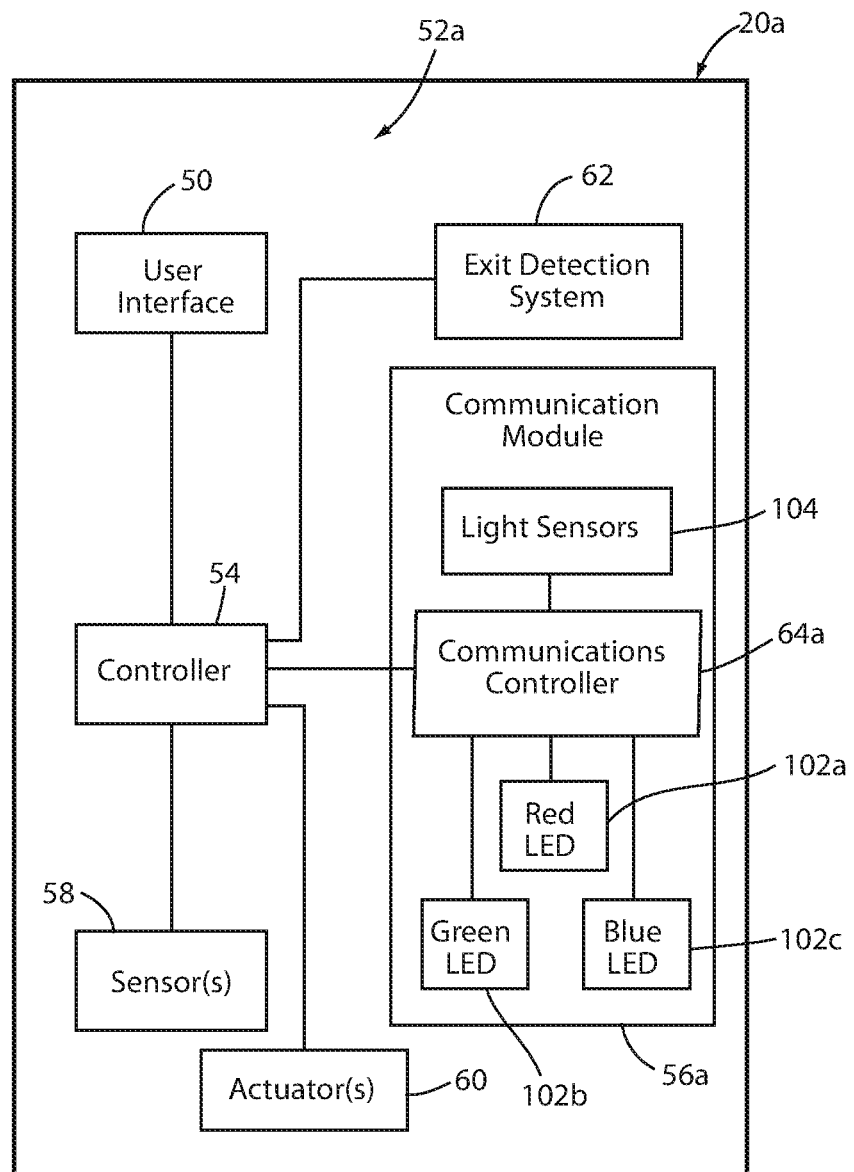
FIG. 7 is a block diagram of a patient support apparatus according to another embodiment of the disclosure.

FIG. 7 illustrates another embodiment of a patient support apparatus 20a according to the present disclosure. Patient support apparatus 20a is usable with any of the communication systems 70, 70a, 70b, and/or 70c discussed herein, as well as still other communication systems. Patient support apparatus 20a includes a number of components and/or features that are the same as patient support apparatus 20. Those components or features that are common are labeled with the same reference numbers used to describe patient support apparatus 20, and unless otherwise explicitly stated below, operate in the same manner or provide the same function as previously described. Those components or features that are different from patient support apparatus 20 are provided with a new reference number and described in more detail below.

Patient support apparatus 20a includes a modified communication module 56a that is adapted to communicate by using visible light. This visible light communication is used either in lieu of, or in addition to, the RF communication methods discussed above. In the embodiment shown in FIG. 7, communication module 56a includes a communications controller 64a that controls at least one red Light Emitting Diode (LED) 102a, at least one green LED 102b, and at least one blue LED 102c. Communications controller 64a is also in communication with one or more light sensors 104. In one embodiment, communication module 56a communicates with one or more visible light receivers (not shown) positioned within a visible light range of patient support apparatus 20a by using color shift keying. Such color shift keying communication takes place, in at least one embodiment, in accordance with the standards set forth in IEEE 801.15.7, although other types of color shift keying may be used.

In general, communication controller 64a modulates the intensity of the red, blue, and/or green light emitted by LEDs 102a-c in accordance with the data to be transmitted. The light from the LEDs 102 is mixed together when emitted from patient support apparatus 20a. By changing the relative composition of the red, blue, and/or green light, the color emitted by the patient support apparatus 20a is modulated. The modulations in the color are detected by one or more visible light receivers positioned within the room of patient support apparatus 20a (or elsewhere where the emitted visible light can be detected). The receivers detect and decode the color modulations and convert them into electrical signals corresponding to the message transmitted from communication module 56a. Each receiver, in some embodiments, is coupled to the LAN 74 by a wired or wireless communication channel. Visible light messages from patient support apparatuses 20a can therefore be converted to conventional electrical signals that are forwarded to LAN 74, including, but not limited to, patient support apparatus server 88. Communication module 56a therefore allows transmitting messages using visible light for at least one link of the communication pathway between patient support apparatuses 20a and a destination, such as LAN 74 and/or enterprise server 86.

Patient support apparatuses 20a also include a light sensor 104. Light sensor 104 detects visible light communications that are transmitted from one or more visible light transmitters (not shown) positioned within the room. Light sensors 104 thereby give communications module 56a the ability to communicate bidirectionally using visible light.

In other embodiments, communication module 56a is modified to transmit messages via visible light using on-off keying instead of color shift keying. Such on-off keying may represent a logic zero state by turning the LED off and on in succession (e.g. 01) and the logic one state by turning the LED on and off in succession (e.g. 10), thereby ensuring that the duty cycle of the light remains at 50 percent regardless of the message contents. Other types of on-off keying protocols may be used. In still other embodiments, communications module 56a may transmit messages by modulating the intensity of light emitted by a single LED (or a group of LEDs having only a single color) in accordance with the message to be transmitted. That is, instead of modulating the overall color produced by one or more LEDs, communication module 56a may communicate by changing the intensity of only a single color of emitted light. Still other types of visible light communication may be used.

Patient support apparatus 20a is usable with any of the communication systems 70 discussed above where the patient support apparatuses forward message to, or receive messages from, an access point 82. In such instances, one or more access points 82 may be replaced with one or more visible light access points that are in communication with, and provide access to, LAN 74. Alternatively, patient support apparatuses 20a may be modified to include both RF wireless communication and visible light communication. In such modified embodiments, patient support apparatuses 20a choose which form of wireless communication to use for a given message based upon the content of the message, the intended recipient of the message, the receiver(s) that are currently within communication range, and/or other factors.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus for use in a healthcare facility having a local area network with a wireless access point, a server coupled to the local area network, and at least one network appliance adapted to communicate with both the local area network and a device remote from the patient support apparatus, the patient support apparatus comprising:
    a support surface adapted to support a patient thereon;
    a wireless transmitter adapted to transmit data to the server via a first path or a second path, the first path including the device remote from the patient support apparatus but excluding the wireless access point, the second path including the wireless access point but excluding the device remote from the patient support apparatus, the first and second paths each extending all of the way from the patient support apparatus to the server; and
    a controller adapted to control when the wireless transmitter transmits data from the patient support apparatus to the server via the first path and when the wireless transmitter transmits data to the server via the second path.

2. The patient support apparatus of claim 1 further including a receiver in communication with the controller wherein the controller is adapted to transmit the data via the second path when the receiver detects a wireless signal from the wireless access point.

3. The patient support apparatus of claim 1 wherein the wireless transmitter is an RF transmitter adapted to transmit in at least one of the following frequency bands: 28 Gigahertz, 37 Gigahertz, and 39 Gigahertz.

4. The patient support apparatus of claim 1 wherein the controller is adapted to append an IP address to the data corresponding to an Internet-accessible server in communication with the network appliance, and wherein the device remote from the patient support apparatus is a receiver coupled to a cell phone tower, the receiver in communication with the Internet-accessible server.

5. The patient support apparatus of claim 1 wherein the device remote from the patient support apparatus is an Internet-accessible server positioned outside of the healthcare facility and in communication with the network appliance, and the controller is adapted to append an IP address to the data corresponding to the Internet-accessible server, the Internet-accessible server forwarding the data to the server via the network appliance.

6. The patient support apparatus of claim 1 further comprising a visible light emitter wherein the controller is further adapted to send the data to the device remote from the patient support apparatus using visible light.

7. The patient support apparatus of claim 1 wherein the data includes at least one of the following: a status of a brake of the patient support apparatus, a status of a siderail of the patient support apparatus, a weight of an occupant of the patient support apparatus, a height of a support surface of the patient support apparatus, and a state of an exit detection system of the patient support apparatus.

8. The patient support apparatus of claim 1 wherein the server is a patient support apparatus server adapted to share a subset of the data with another server coupled to the local area network.

9. The patient support apparatus of claim 8 wherein the another server is one of an Electronic Medical Records (EMR) server and an Admission, Discharge and Tracking (ADT) server.

10. The patient support apparatus of claim 1 wherein the data includes at least one of the following: (a) a number of times a motor on the patient support apparatus has been operated; (b) a current draw of a motor on the patient support apparatus; (c) a temperature of a component on the patient support apparatus; (d) an error signal from a component of the patient support apparatus; (e) a position of an actuator of the patient support apparatus; and (f) a software and/or hardware version of a component of the patient support apparatus.

11. The patient support apparatus of claim 1 wherein the controller appends a first address to the data when sending the data via the first path and appends a second address to the data when sending the data via the second path.

12. The patient support apparatus of claim 11 wherein the controller further appends a third address to the data, the third address corresponding to the server.

13. The patient support apparatus of claim 11 wherein the network appliance is one of a router and a gateway.

* * * * *